United States Patent
Visuri et al.

(12) 
(10) Patent No.: US 6,368,318 B1
(45) Date of Patent: *Apr. 9, 2002

(54) OPTO-ACOUSTIC RECANILIZATION DELIVERY SYSTEM

(75) Inventors: Steven R. Visuri, Livermore; Luiz B. Da Silva, Danville; Peter M. Celliers, Berkeley; Richard A. London, Orinda; William Benett, Livermore; Kathryn Broughton, Berkeley; Victor Esch, San Francisco, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/012,379

(22) Filed: Jan. 23, 1998

(51) Int. Cl.$^7$ ................................................ A61B 18/18
(52) U.S. Cl. ............................... 606/7; 606/12; 606/15; 606/17
(58) Field of Search .................. 606/7, 10, 11, 606/12, 15, 16, 17

(56) References Cited

U.S. PATENT DOCUMENTS

| 3,858,577 A | 1/1975 | Bass et al. |
| 3,866,599 A | 2/1975 | Johnson |
| 4,204,528 A | 5/1980 | Termanini |
| 4,207,874 A | 6/1980 | Choy |

(List continued on next page.)

FOREIGN PATENT DOCUMENTS

| CA | 2104239 | 2/1994 |
| DE | 3833361 | 4/1990 |

(List continued on next page.)

OTHER PUBLICATIONS

"Laser Surgery in Enclosed Spaces: A Review", Macruz et al., Lasers in Surgery and Medicine, vol. 5, No. 3, 1985, pp. 199–218.

"Multifiber Optically–Shielded Catheter for Laser Angiosurgery", Goth et al., Optical Fibers in Medicine II, vol. 713, Sep. 17–19, 1986, pp. 58–63.

(List continued on next page.)

Primary Examiner—Linda C. M. Dvorak
Assistant Examiner—David M. Ruddy
(74) Attorney, Agent, or Firm—John P. Wooldridge; Alan H. Thompson

(57) ABSTRACT

Fiber delivered laser pulses emulsify thrombus by mechanical stresses that include a combination of pressure, tension and shear stress. Laser radiation is delivered to the locality of a thrombus and the radiation is absorbed by blood, blood dot, or other present materials. The combination of a leading pressure wave and subsequent vapor bubble cause efficient, emulsification of thrombus. Operating the laser in a low average power mode alleviates potential thermal complications. The laser is operated in a high repetition rate mode to take advantage of ultrasound frequency effects of thrombus dissolution as well as to decrease the total procedure time. Specific parameter ranges for operation are described. The device includes optical fibers surrounding a lumen intended for flow of a cooling agent. The fibers may be arranged concentrically around the lumen to deliver radiation and heat over as large an area as possible. An alternative design approach incorporates the optical fibers into the wall of the guiding catheter and utilizes the catheter lumen as the cooling channel. An eccentric tip enables rotation of the device to address all parts of the vasculature. The eccentricity can be provided via a variety of means: spring dip, balloon, protrusion, etc.

48 Claims, 4 Drawing Sheets

U.S. PATENT DOCUMENTS

| | | | |
|---|---|---|---|
| 4,309,998 A | 1/1982 | Aron nee Rosa et al. | |
| 4,418,688 A | 12/1983 | Loeb | |
| 4,587,972 A | 5/1986 | Morantte, Jr. | |
| 4,681,104 A | 7/1987 | Edelman | |
| 4,686,979 A | 8/1987 | Gruen et al. | |
| 4,732,448 A | 3/1988 | Goldenberg | |
| 4,782,819 A * | 11/1988 | Adair | 606/10 |
| 4,830,460 A | 5/1989 | Goldenberg | |
| 4,832,023 A | 5/1989 | Murphy-Chutorian | |
| 4,834,093 A | 5/1989 | Littleford et al. | |
| 4,844,062 A | 7/1989 | Wells | |
| 4,848,336 A | 7/1989 | Fox et al. | |
| 4,850,351 A | 7/1989 | Herman et al. | |
| 4,852,567 A | 8/1989 | Sinofsky | |
| 4,878,492 A | 11/1989 | Sinofsky et al. | |
| 4,913,142 A | 4/1990 | Kittrell et al. | |
| 4,950,266 A | 8/1990 | Sinofsky | |
| 5,026,367 A | 6/1991 | Leckrone et al. | |
| 5,032,123 A | 7/1991 | Katz et al. | |
| B1 4,800,876 | 7/1991 | Fox et al. | |
| 5,109,859 A | 5/1992 | Jenkins | |
| 5,188,632 A | 2/1993 | Goldenberg | |
| 5,188,634 A | 2/1993 | Hussein et al. | |
| 5,192,278 A | 3/1993 | Hayes et al. | |
| 5,203,779 A * | 4/1993 | Muller et al. | 606/7 |
| 5,242,454 A | 9/1993 | Gundlach et al. | |
| 5,250,045 A | 10/1993 | Bohley | |
| 5,251,640 A | 10/1993 | Osborne | |
| 5,254,112 A | 10/1993 | Sinofsky et al. | |
| 5,261,904 A | 11/1993 | Baker et al. | |
| 5,263,952 A | 11/1993 | Grace et al. | |
| 5,290,280 A * | 3/1994 | Daikuzono | |
| 5,324,255 A | 6/1994 | Passafaro et al. | |
| 5,334,171 A | 8/1994 | Kaldany | |
| 5,350,375 A | 9/1994 | Deckelbaum et al. | |
| 5,370,608 A | 12/1994 | Sahota et al. | |
| 5,377,683 A | 1/1995 | Barken | |
| 5,380,273 A | 1/1995 | Dubrul et al. | |
| 5,395,361 A | 3/1995 | Fox et al. | |
| 5,397,301 A | 3/1995 | Pflueger et al. | |
| 5,415,653 A * | 5/1995 | Wardle et al. | |
| 5,429,604 A | 7/1995 | Hammersmark et al. | |
| 5,454,807 A | 10/1995 | Lennox et al. | |
| 5,462,544 A | 10/1995 | Saksena et al. | |
| 5,466,234 A | 11/1995 | Loeb et al. | |
| 5,470,330 A | 11/1995 | Goldenberg et al. | |
| 5,472,406 A | 12/1995 | de la Torre et al. | |
| 5,484,433 A | 1/1996 | Taylor et al. | |
| 5,514,128 A | 5/1996 | Hillsman et al. | |
| 5,662,590 A | 9/1997 | de la Torre et al. | |
| 5,700,243 A | 12/1997 | Narciso, Jr. | |
| 5,746,738 A * | 5/1998 | Cleary et al. | |
| 5,944,687 A | 8/1999 | Benett et al. | |
| 6,033,371 A | 3/2000 | de la Torre et al. | |
| 6,106,546 A | 8/2000 | Gregory | |

FOREIGN PATENT DOCUMENTS

| | | |
|---|---|---|
| EP | 0144764 | 6/1985 |
| GB | 2208807 | 4/1989 |
| WO | 9216140 | 10/1992 |
| WO | 93146879 | 5/1993 |
| WO | W9315672 | 8/1993 |
| WO | W9316407 | 8/1993 |
| WO | W9408523 | 4/1994 |
| WO | W9739690 | 10/1997 |
| WO | WO9916366 | 4/1999 |
| WO | WO9920189 | 4/1999 |

OTHER PUBLICATIONS

"Engineering of a Multifiber Catheter with an Optical Shield for Laser Angiosurgery", Proceedings of the Ninth Annual Conference of the IEEE Engineering in Medicine and Biology Society, Nov. 13–16, 1987, pp. 200–202.

"Initial Clinical experience with a new Pulsed Dye Laser Device in Angioplasty of Limb Ischemia and Shunt Fistula Obstructions", European Journal of Radiology, vol. 14, No. 1, Jan.–Feb. 1992, pp. 72–76.

* cited by examiner

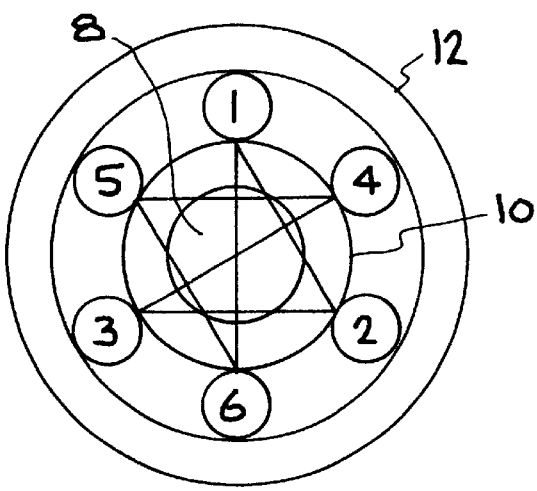
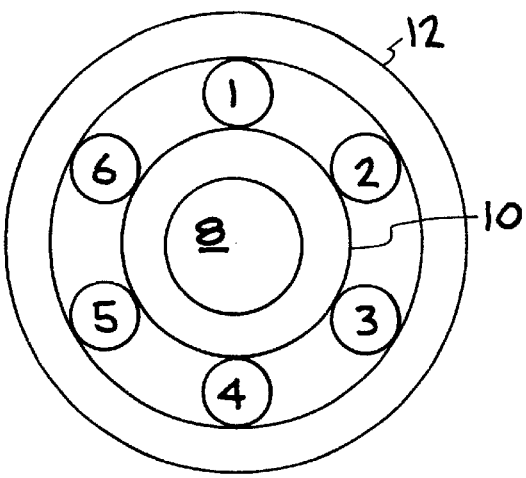
FIG. 3A                FIG. 3B
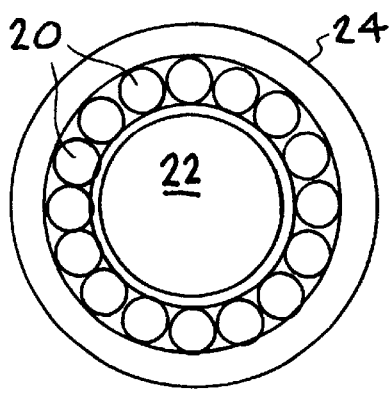
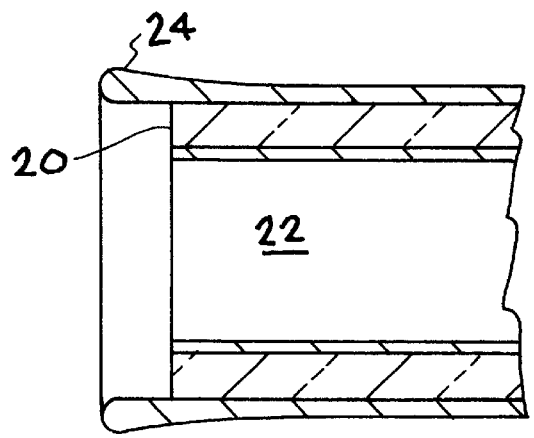
FIG. 4A                FIG. 4B
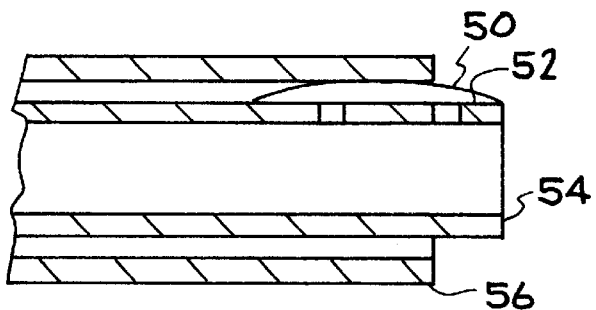
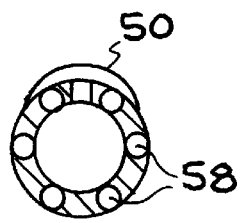
FIG. 5A                FIG. 5B

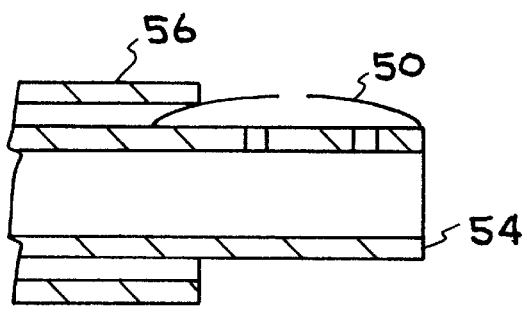 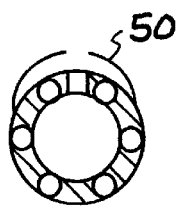 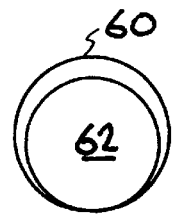
FIG. 5C  FIG. 5D  FIG. 5E
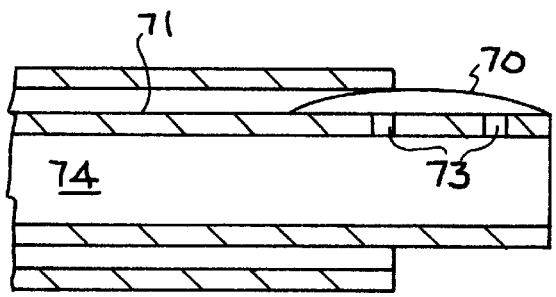 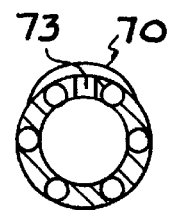
FIG. 6A  FIG. 6B
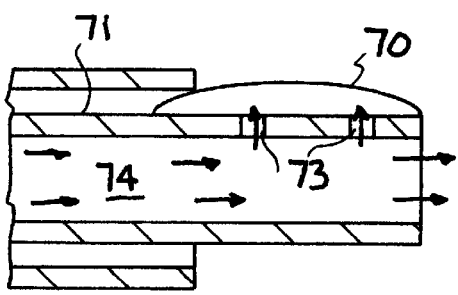 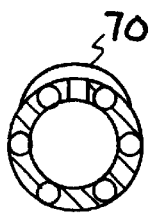 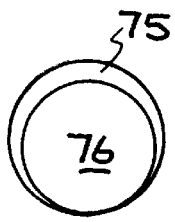
FIG. 6C  FIG. 6D  FIG. 6E

OPTO-ACOUSTIC RECANILIZATION DELIVERY SYSTEM

The United States Government has rights in this invention pursuant to Contract No. W-7405-ENG48 between the United States Department of Energy and the University of California for the operation of Lawrence Livermore National Laboratory.

BACKGROUND OF THE INVENTION

1. Field of the Invention

The present invention is directed to the removal of blockages in tubular tissues and organs, and more specifically, it relates to the removal of intravascular occlusions such as atherosclerotic plaque or thrombus.

2. Description of Related Art

Ischemic strokes are caused by the formation or lodging of thrombus in the arterial network supplying the brain. Typically these occlusions are found in the carotid artery or even smaller vessels located still higher in the cranial cavity. Interventional cardiologists and vascular surgeons have devised minimally invasive procedures for treating these conditions in the vasculature elsewhere in the body. Among these treatments is ultrasound angioplasty whereby a microcatheter is directed to the site of an occlusion. An ultrasonic transducer is coupled to a transmission medium that passes within the catheter and transmits vibrations to a working tip at the distal end in close proximity to the occlusion. Ultrasonic catheters for dissolving atherosclerotic plaque and for facilitating clot lysis have been described previously. Improvements on these inventions have concentrated on improving the operation or function of the same basic device (See Pflueger et al., U.S. Pat. No. 5,397,301). The vibrations coupled into the tissues help to dissolve or emulsify the clot through various ultrasonic mechanisms such as cavitation bubbles and microjets which expose the clot to strong localized shear and tensile stresses. These prior art devices are sometimes operated in conjunction with a thrombolytic drug. A radiographic contrast agent is often used to facilitate visualization.

The ultrasonic catheter devices all have a common configuration in which the source of the vibrations (the transducer) is external to the catheter. The vibrational energy is coupled into the proximal end of the catheter and transmitted down the length of the catheter through a wire that can transmit the sound waves. There are associated disadvantages with this configuration: loss of energy through bends and curves with concomitant heating of the tissues in proximity; the devices are not small enough to be used for treatment of stroke and are difficult to scale to smaller sizes; it is difficult to assess or control dosimetry because of the unknown and varying coupling efficiency between the ultrasound generator and the distal end of the catheter. Dubrul et al., U.S. Pat. No. 5,380,273, attempts to improve on the prior art devices by incorporating advanced materials into the transmission member. Placement of the ultrasonic transducer itself at the distal end of the catheter has been impractical for a number of reasons including size constraints and power requirements.

A related method for removing occlusions is laser angioplasty in which laser light is directed down an optical fiber to impinge directly on the occluding material. Laser angioplasty devices have been found to cause damage or destruction of the surrounding tissues. In some cases uncontrolled heating has lead to vessel perforation. The use of high energy laser pulses at a low or moderate repetition rate, e.g. around 1 Hz to 100 Hz, results in non-discriminatory stress waves that significantly damage healthy tissue or result in insufficient target-tissue removal when the laser parameters are adjusted such that healthy tissue is not affected. Use of pulses of high energy laser light to avoid thermal heating has been found to cause damage through mechanisms associated with large cavitation bubbles and shock waves that rupture or otherwise adversely affect the tissue.

SUMMARY OF THE INVENTION

It is an object of the present invention to provide means for dissolution of vascular occlusions with low energy laser pulses at high repetition rates for generation of ultrasonic excitation in the fluids in close proximity to the occlusion.

It is another object of the present invention to provide techniques for removing clot material from the cerebrovasculature.

Another object of the invention is to provide techniques for removal of occlusions from the body.

Still another object of the present invention is to provide techniques for removing occlusions from the cerebrovasculature and the body without causing collateral damage to the vessel.

In the Opto-Acoustic Recanilization or Recanalization (OAR) device of the present invention, fiber delivered laser pulses emulsify thrombus by mechanical stresses that include a combination of pressure, tension and shear stress. High pressures primarily effect the small volume of material in which the laser light is absorbed, while the tensile and shear stresses effect a larger surrounding volume. The effectiveness of emulsification depends on the characteristics of the stresses-their magnitude, time-dependence and type (i.e. compressive, tensile or shear), and the response of the thrombus to such stresses. In general, the OAR device has been designed to maximize the mass of thrombus emulsified per unit laser energy. This is important for three reasons, (i) to minimize the required laser energy and thereby the laser cost, (ii) to minimize the time it takes to emulsify a given clot volume and (iii) to minimize the waste heat left in the tissue, which may lead to undesirable damage.

The present invention includes a laser coupled to an optical fiber delivery system and means for delivery of a cooling agent. The present design has evolved from a combination of experimental and theoretical modeling results. In concept, the laser radiation is delivered to the locality of a thrombus, the radiation is absorbed by blood, blood clot, or other present materials. The combination of a leading pressure wave and subsequent vapor bubble cause efficient emulsification of thrombus. The laser is operated in a low average power mode such that potential thermal complications are alleviated. The laser is operated in a high repetition rate mode to take advantage of ultrasound frequency effects of thrombus dissolution as well as to decrease the total procedure time. Specific parameter ranges for operation are described.

The delivery system for the OAR device of the present invention is intended to traverse through commercially available vascular catheters and must have the flexibility to traverse tortuous pathways and the diameter to pass smoothly through a small lumen. The device includes optical fibers surrounding a central lumen intended for flow of a cooling agent. The fibers may be arranged concentrically around the central lumen to deliver radiation and subsequent thermal energy over as large an area as possible. An alternative design approach incorporates the optical fibers into the wall of the guiding catheter and utilizes the catheter lumen as the cooling channel.

The distal tip firing pattern can be chosen to create a number of effects. A star pattern would serve to move the thermal energy in each consecutive pulse packet to a location far from the previous packet, and therefore never concentrate the heat. A circular pattern may be beneficial if there is a mechanical advantage to consecutively impacting adjacent areas. Additionally the fibers tips could be pointed towards or away from the central lumen to target specific areas.

Delivery of a pulse of laser radiation into an absorbing material can result in a significant movement of the fiber delivery system. This mechanical motion can be used to further disrupt thrombus. Fibers can be beveled or angled to aim the effect (primarily the shock wave) to produce a lateral deviation of the tip upon delivery of laser radiation, or promote a fluid jetting directional phenomenon. Fiber angling and/or particular firing patterns can be employed to produce agitation at the tip. In addition, the cooling agent can be employed to produce similar phenomena. The cooling tip can be made into a nozzle that would allow the coolant to jet in particular patterns or directions. In another configuration, a shrouded tip prevents the fibers from coming into contact with vessel wall yet enables interaction with blood or thrombus.

An eccentric tip may allows rotation of the device to address all parts of a vessel. A spring affixed to the outer wall of the delivery system is held collapsed with a slight compressive force within the target catheter or similar system. The spring pops up when the delivery system is extended away from target catheter. As the catheter is rotated, an area greater than the area of the catheter is covered.

An eccentric tip is provided in another device by attaching a bladder to the side of the delivery device. Leak paths through the wall of delivery device are provided to present an unobstructed path between the central lumen and the bladder. When no cooling flow or other flow is passed though central lumen, the bladder remains deflated. Upon the extension of the delivery system, and providing flow though the central lumen and through the leak paths, a pressure is induced in the bladder, causing it to inflate and provide an eccentric geometry.

Eccentricity is provided in another embodiment by an off-center (asymmetric) construction of the fiber array and flow tube within the area of the delivery system. Although this embodiment provides an alternate geometry to achieve eccentricity, rotation of the catheter will not produce an increase in the total area covered. A trimmed corner of the delivery system, which also contains an off-center construction of the fiber array and the flow tube within delivery system allows flow to force the assembly to one side. The slight angle induced in the fluid flow forces the tip of the catheter or delivery system to bend.

The delivery device generally must traverse through a standard catheter traveling through a tortuous path, Primarily at the distal portion, the device must be flexible, with good column strength for ease of pushing. The device may be constructed with fibers (optical or other) incorporated into the wall of the delivery system or catheter. These embedded fibers can be utilized for desirable characteristics, such as cross-woven proximally for strength, and straight threading distally for maximal flexibility. In another configuration, the fibers "float" freely within the central lumen throughout the body of the catheter and are fixed at the distal tip. This embodiment allows the catheter diameter to be reduced if desired and allows for increased flexibility.

Current techniques for removal of clot material in the cerebrovasculature involve either doing nothing in hopes the clot resolves on its own or using pharmacologic thrombolytic agents. The major complication with thrombolytic drugs is the potential for induced hemorrhage. Secondly, thrombolytics do not work satisfactorily on all clots. This invention is a laser-based device for mechanical disruption of thrombus. Problems encountered with laser-based approaches, and solved by this invention, arise from the fact that optical to mechanical conversion is inefficient. Delivering too much average power into vessels can damage the vessels and also thermally alter blood and clot material, making the clot more difficult to remove. The present invention includes an optimization of the basic underlying phenomena and the system related parameters of fiber size, repetition rate, cooling flow, etc.

BRIEF DESCRIPTION OF THE DRAWINGS

FIG. 3A shows the distal tip of a delivery system using a star firing pattern.

FIG. 3B shows the distal tip of a delivery system using a circular firing pattern.

FIG. 4A shows a front view of a shrouded distal tip.

FIG. 4B shows a side view of a shrouded distal tip.

FIGS. 5A–E show an eccentric tip with a spring clip.

FIGS. 6A–E show an eccentric tip with an inflatable balloon/bladder.

DETAILED DESCRIPTION OF THE INVENTION

The present invention includes several embodiments of delivery systems capable of performing, opto-acoustic thrombolysis (OAT), also termed opto-acoustic recanailization or recanalization (OAR). OAT is described in U.S. patent application Ser. No. 08/639,017 titled "Opto-Acoustic Thrombolysis" and U.S. patent application Ser. No. 08/955, 858 titled "Photoacoustic Removal of Occlusions From Blood Vessels" respectively, the disclosures of which are both incorporated herein by reference.

Figure 1:
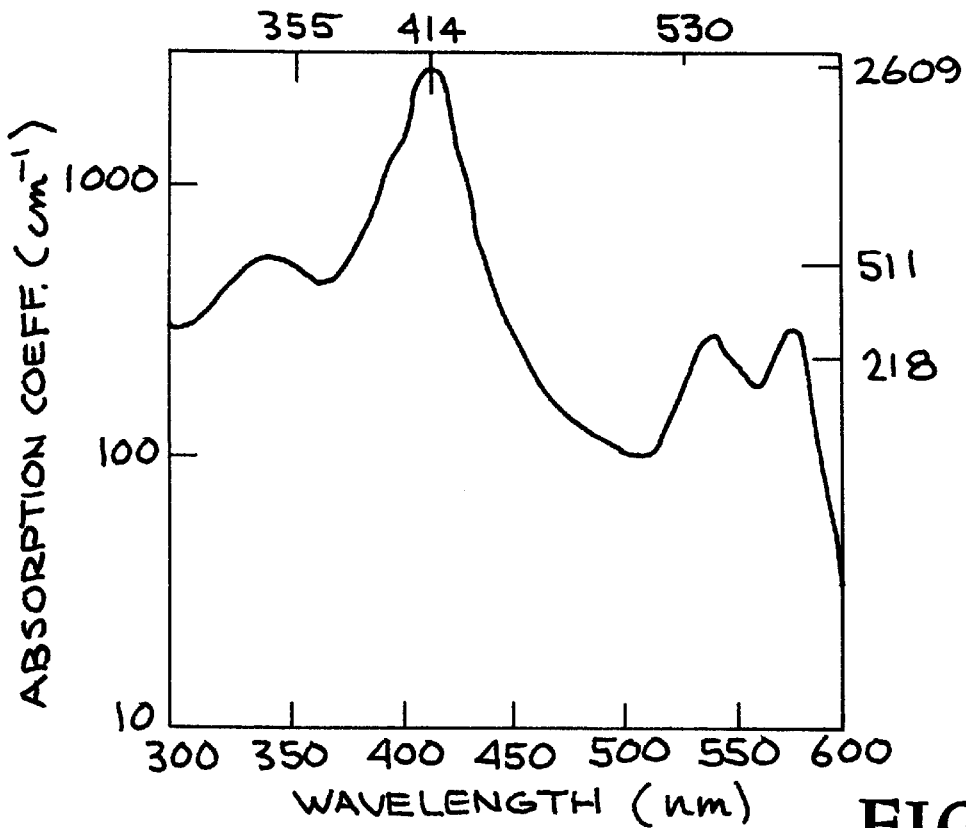
FIG. 1 shows absorption coefficient of whole blood versus wavelength.

In the processes of OAT, laser light is absorbed in a nearly cylindrical volume of diameter approximately equal to the fiber diameter and length approximately equal to the laser absorption length. When the medium is thrombus, absorption is mainly due to blood and the absorption length is a strong function of laser wavelength as shown in FIG. 1. The wavelengths and absorption coefficients of doubled and tripled Nd:YAG are explicitly labeled, as are those of the absorption maximum. As discussed further below, it is desirable to make the absorption volume fairly small and therefore a small fiber diameter (50 $\mu$m) and a laser wavelength giving a short absorption length have been chosen. A suitable laser wavelength is 532 nm, which is both readily available with frequency-doubled Nd-YAG lasers as well as highly absorptive (absorption length=50 µm in blood). The absorbed laser energy heats the medium. For short duration pulses, the expansion of the heated medium launches acoustic waves which generate the stresses responsible for emulsification. The character of the acoustic waves depends on two system parameters: the laser pulse length relative to the stress confinement time ($=t_L$), and the energy density of absorbed laser light ($e_L$). The stress confinement time is defined as the time for a sound wave to emerge from the center of the heated region, which is equal to the radius of the volume divided by the sound speed. Since the sound speed in clot is approximately that of water, $1.5\times10^5$ cm/s, the stress confinement time is approximately 17 ns for a volume having a 25 µm radius.

For pulses shorter than the stress confinement timescale the heating occurs at nearly constant density and high positive pressures are created. The heated volume then expands, launching both fast and slow acoustic waves into the surrounding medium. The fast wave is emitted in a time approximately equal to the stress confinement time. The strength of the fast wave is determined both by the pulse duration and the energy density (laser energy/absorption volume). The wave will be strongest for pulse durations much shorter than the stress confinement time. For pulses long compared to the stress confinement time, the medium expands nearly isobarically during the pulse and never attains high pressures. Thus to obtain the maximum strength fast wave, a very short pulse is necessary, substantially less than 17 ns for a 25 µm radius heated region. Numerical calculations indicate that maximum strength fast waves are achieved for pulses less than 5 ns, while for 17 ns pulses, the strength is approximately 60% of the value achieved for shorter pulses.

Figure 2:
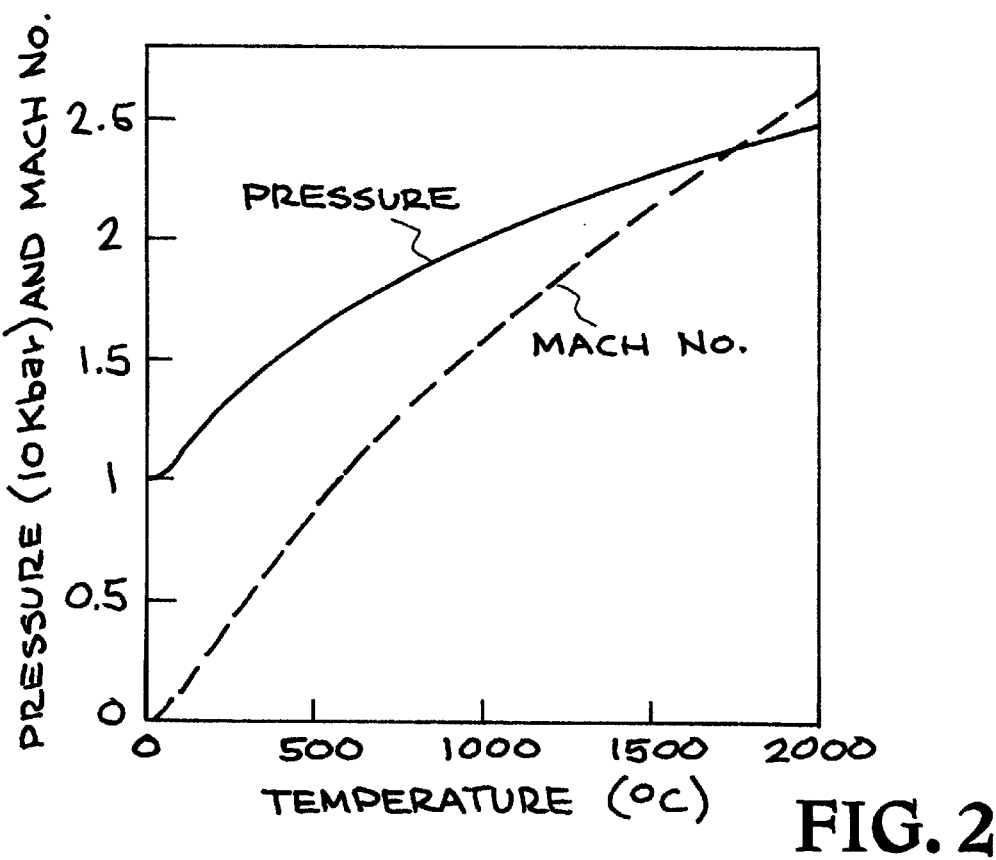
FIG. 2 shows pressure and shock Mach number versus heated temperature.

The energy density of absorbed laser light determines the maximum temperatures and pressures achieved in the heated volume. For short pulses, the laser energy gets converted into thermal energy resulting in a temperature, $T=T_i+e_L/C_V$, where $T_i$ is the initial temperature and $C_V$ is the specific heat at constant volume which is assumed to be constant, but more detailed analysis has considered its variation with temperature. For water, $C_V=4.2$ J/g/C, a value also typical for soft clot. The pressure generated (which depends on the temperature) has been calculated with the NIST equation of state for water and is depicted in FIG. 2. An initial temperature before heating of 25° C. is assumed. The pressure is in units of $10^4$ bar. After the short laser pulse, the heated material begins to expand and its pressure drops. Initially, the pressure drops very rapidly, because of the very large slope of the pressure-density function of condensed matter (both liquids and solids). If the temperature is below the boiling point, the medium will remain mostly liquid and the expansion will not proceed to low density. The interior pressures return to ambient (or even negative) values right away. This case produces only a fast wave and not a slow wave. If the temperature is well above the boiling point, the water content of the absorbing media will become vapor as the expansion occurs. This vapor maintains a high pressure for much larger expansions than liquid. The continued high pressure produces the slow wave, which is associated with the production of a vapor bubble in the interior of the heated region. Thus, heating well above boiling by short pulses produces both fast and slow waves.

In the case of slow heating (i.e., long laser pulses compared to the stress confinement time), high pressures are never reached because the heated medium expands during the pulse. In this case, only a slow wave is produced, with a duration of the order of the pulse length. For deposited energy densities above the critical value a vapor bubble will be produced. It is easy to estimate the size of the vapor bubble by assuming that all of the energy above the critical value goes into producing vapor at the ambient pressure and the boiling point at that pressure (100° C. for P=1 bar). From such an analysis, it has been found that the efficiency of producing vapor bubbles (defined as their volume divided by the laser energy) grows with energy density.

For short pulses, the strength of the fast wave is defined by its pressure. The wave propagates at, or above, the sound speed in the ambient medium. The strength drops with distance from the heated volume. To be most effective in the emulsification, the strength needs to be large. Large pressure waves generally evolve into shock waves that propagate at supersonic speeds into a material. The OAR device with short pulses and high energy densities produces such fast shock waves. The strength of a shock is usually measured by its Mach number, defined as the shock speed relative to the sound speed in the unshocked material. To find the Mach number, a simple fit is made to the adiabatic equation of state (EOS) of water and a standard shock hydrodynamic formula. The water EOS is $$P = A(\rho/\rho_0)^\gamma - B,$$

where P is the pressure, $\rho$ the density and $\rho_0$ the density at standard conditions (1.0 gm/cc). The constants are A=3000 atm, B=(A−1 atm), and g=7. The formula for the Mach number of the shock wave is:

$$M^2 = [(g-1)+(g+1)P'/P_0']/2\, g,$$

where $P'=P+B$, and $P_0'=P_0+B$, and $P_0$ is the ambient pressure.

Using these formulae, the shock Mach number is shown in FIG. 2 as a function of heated temperature. Experiments have shown that the OAR device works in the range 40 to 7000 J/g deposited laser energy density, for which the Mach numbers are 1.2 to 2.0. This range of operation produces strong shocks which significantly emulsify thrombus.

In summary, short pulse durations create shock waves (velocity>sound speed), and with sufficient energy, vapor bubbles are produced, which drive the material emulsification process. The combination of the shock wave and the vapor bubble phenomena is preferable to produce efficient emulsification. The actual energy present in the shock wave is very small compared to the vapor bubble, but experimentally the shock wave is critical to improved emulsification.

To create a shock wave, energy must be deposited into a volume in a time shorter than the resultant increased pressure can relax, i.e. before the volume can expand and relieve the increased pressure. For a fixed volume, increased temperature will result in increased pressure. The stress relaxation process proceeds at the speed of sound in the medium. Thus, the energy must be deposited in a time less than the sound propagation time across the smallest dimension of the deposition. For the irradiation geometry proposed, the smallest dimension is approximately 25 µm, which is the optical fiber radius and also the approximate penetration depth. The resultant stress confinement duration is approximately 17 ns ($25\times10^{-6}$ m/1500 ms$^{-1}$).

Energy/pulse emitted by the laser is preferably in the range of 50 µJ–250 µJ. A lower limit of 50 µJ is set by the threshold for forming a vapor bubble in a water based system with similar absorption characteristics as blood. The upper limit of approximately 250 µJ is set by the fragility of the emitting optical fiber. A strong stress wave is created when the laser radiation is absorbed into the media. The magnitude of the stress wave is largely dependent on the energy/pulse. The stress wave reflects back into the fiber and can be shown to damage unprotected fiber tips using energies above 250 µJ.

The wavelength used in conjunction with the device should be chosen to achieve the desired strong absorption in the intended absorbing media. Possible absorbers could include blood, thrombus, saline, contrast media, exogenous absorbing dyes or any combination of the aforementioned. The desired effect consists of creation of a leading stress wave followed by a vapor bubble. To maximize efficiency in this regime it is desirable to maximize energy density. Choosing a highly absorbing wavelength decreases penetration depth and increases energy density. However, one must also consider other required laser parameters such as energy, pulse duration, and repetition rate when choosing the highest absorbing wavelength. Presently the device operates at 532 nm, which is highly absorbed in blood (see FIG. 1, absorption coefficient≈200 $cm^{-1}$) and easily produced by frequency doubled Nd:YAG lasers.

As previously discussed, the efficiency of operation is often maximized by maximizing the energy density. Specifically, if a vapor bubble of finite dimension is desired, the amount of energy needed to produce such a bubble consists of: heating the material to its boiling point, supplying the latent heat of vaporization, and supplying the energy to expand the bubble. The required energy can be reduced by decreasing the penetration depth and spot size of the radiation which determine the volume. For fiber delivered energy, the spot size is largely determined by fiber diameter. The invention presently consists of delivering the radiation via 50 µm optical fibers which allow for easy laser coupling and power delivery while minimizing spot size. Small fiber size is also beneficial for device flexibility.

If a significantly larger bubble is required for a given (small) fiber, it is not possible in general to just turn up the energy because of the fiber damage threshold. Thus, fiber size must be increased at some point, forcing a less efficient generation of a given larger bubble size. It is better to attack a surface cross section with 10 small fibers at a high repetition rate, with low energies, via multiplexing, than one big (10 times the area) fiber, at 1/10 repetition rate which will require more than 10 times the energy per pulse, and will produce a vapor bubble big enough to risk collateral damage, and will also cause average power problems.

The repetition rate of the laser should be in the range of 1 kHz to 50 kHz. Choice of repetition rate is determined by desired emulsification rate and frequency dependent effects. If a finite amount of material is emulsified with each laser pulse, irrespective of pulse repetition frequency, then emulsification rate will increase linearly with pulse repetition frequency. However, there may be frequency dependent effects of emulsification wherein emulsification rates may not behave linearly and may be optimal within a particular frequency range. Frequency has known implications in material fatigue and yield strengths. Typically, yield strength increases as the strain rate increases. Additionally thrombus may demonstrate 'resonant' frequencies, such that a specific narrow range of frequencies may exhibit heightened emulsification. Finally, the repetition rate may be limited by the vapor bubble lifetime; it may be advantageous to begin formation of a vapor bubble immediately upon collapse of the previous bubble and likely not before this time. The repetition rate of the laser should be chosen to capitalize on these phenomena.

Duty cycle determines the average power delivered into a tissue and the duration of a procedure. Duty cycle can be chosen to alleviate thermal complications arising from local heating of tissues. For example, if it is determined that operating at 5 kHz, 200 µJ/pulse is optimal, this results in delivering 1 W of power. This may be too large of a thermal load to deliver to a small vessel. Duty cycling, for example running 1 ms on/2 ms off, and repeating, would limit the power to a more manageable 0.3 W.

The OAR process presently uses 1 ml/min. infusion of isotonic saline or water as a cooling agent but a variety of biocompatible fluids may be used. Cooling flow serves two main purposes: to convectively cool the treatment site and to maintain clean fiber tips for unobstructed delivery of laser radiation. Flow rates should be chosen so as not to overburden the vascular system yet supply sufficient cooling that prevents thermal damage to the neighboring vessel wall.

An embodiment of the OAR process uses a 532 nm wavelength, pulse energy of about 100 µJ in 25 ns pulses at 5 kHz into a 50 micron diameter fiber with an array of 6–12 fibers.

The delivery system for the OAR device of the present invention is intended to traverse through commercially available vascular catheters such as Target Therapeutics' Tracker-18. The device must have the flexibility to traverse tortuous pathways and the diameter to pass smoothly through a lumen of less than 500 µm. As shown in FIGS. 3A and 3B, the device may consist of a plurality of optical fibers 1–6 surrounding a central lumen 8 intended for flow of a cooling agent. Central lumen 8 may be formed of a flexible tubing 10. A central lumen for cooling has the advantage of more uniformly cooling circumferentially-surrounding fibers. The size of the lumen determines the pressure head needed to obtain the desired cooling flow rate. This fact should be considered in design of the delivery device so as not to expose the device to excessive pressures. The number of fibers incorporated into the design depends on multiple factors including size and flexibility limitations of the device. The fibers may be arranged concentrically around the central lumen to deliver radiation and heat over as large an area as possible. The plurality of fibers are surrounded with a flexible tubing 12. An alternative design approach would be to incorporate the optical fibers into the wall of the guiding catheter and utilize the catheter lumen as the cooling channel.

The distal tip firing pattern can be chosen to create a number of effects. A star pattern where, e.g., the laser is pulsed through the individual fibers 1–6, as shown in FIG. 3A would serve to move the thermal energy in each consecutive pulse packet to a location far from the previous packet, and therefore never concentrate the heat. A circular pattern, shown in FIG. 3B, may be beneficial if there is a mechanical advantage to consecutively impacting adjacent areas. Additionally the fibers tips could be pointed towards or away from the central lumen to target areas other than directly forward looking.

Delivery of a pulse of laser radiation into an absorbing material can result in a significant reciprocal force on the fiber delivery system. This force can create mechanical motion that can be used to further disrupt thrombus. Significant mechanical motion of a free fiber tip can be produced to provide nonaxial bubble recoil force. This phenomena can be used with several pulses to accumulate displacement, and a subsequent off period to allow the fiber tip to swing back through zero displacement. This phenomena can be highly resonant and thus enhancable. Fibers can be beveled or angled to aim the effect (primarily the shock wave) to produce a lateral deviation of the tip upon delivery of laser radiation, or promote a fluid jetting directional phenomena. Fiber angling and/or particular firing patterns can be employed to produce agitation at the tip, for example alternating clock-wise and counter-clock-wise directionality to promote agitation similar to a washing machine. In addition, the cooling agent can be employed to produce similar phenomena. The cooling tip can be made into a nozzle that would allow the coolant to jet in particular patterns or directions.

The distal tip of the delivery device may require a special configuration depending on the specific locations and constraints under which it is used. It may be undesirable to have the fiber optic tips in contact with or in very close proximity to (<100 μm) a vessel wall. A shrouded tip (see FIGS. 4A and 4B) could be implemented to prevent the fibers from coming into contact with vessel wall yet enable interaction with blood or thrombus. The fiber optics 20 and cooling channel 22 are recessed within the outer tubing 24.

A possible complication may arise when using a device that is much smaller than its target vessel, such that incomplete clearing of thrombus results. An eccentric tip may solve this problem by allowing a doctor to rotate the device to address all parts of a vessel. The eccentricity can be provided via a variety of means: spring clip, balloon, protrusion, etc. Referring to FIG. 5A, a spring 50 affixed to the outer wall 52 of the delivery system 54 is held collapsed with a slight compressive force within the target catheter 56 or similar system. FIG. 5B shows an end view of the delivery system 54 with fibers 58 and compressed spring 50. FIG. 5C illustrates how the spring 50 pops up when the delivery system 54 is extended away from target catheter 56. The expanded spring 51 is shown in both the side view of FIG. 5C and in the end view of FIG. 5D. As the catheter 56 is rotated, an area 60 greater than the area 62 of the catheter 56 is covered, as shown in FIG. 5E.

An eccentric tip with an inflatable balloon/bladder is illustrated in FIGS. 6A–E. FIG. 6A shows a side view of the device which includes a bladder/balloon 70 attached to the side of delivery device 71. Leak paths 73 through the wall of delivery device 71 are provided to present an unobstructed path between the central lumen 74 and bladder 70. The side view shown in FIG. 6A and the end view shown in FIG. 6B depict the step where no cooling flow or other flow is passed though central lumen 74. In this step, the bladder 70 remains deflated. Delivery system 71 is extended in preparation for the next step. Flow passed though central lumen 74, through leak paths 73 induces pressure in bladder 70 causing it to inflate, as shown in FIGS. 6C and 6D. The inflated bladder 70 provides an eccentric geometry. As the catheter is rotated, the total area 75 is greater than the area 76 of the catheter, as illustrated in FIG. 6E.

Figure 7:
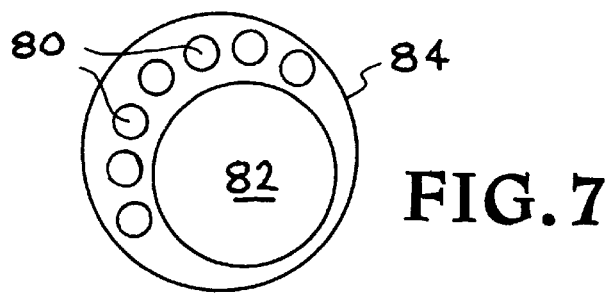
FIG. 7 shows an eccentric tip with an off-center flow tube.

FIG. 7 shows a cross sectional or end view of an eccentric tip with an off-center flow tube. Eccentricity is provided by an off-center (asymmetric) construction of the fiber array 80 and flow tube 82 within the area of the delivery system 84. Although this embodiment provides an alternate geometry to achieve eccentricity, rotation of the catheter will not produce an increase in the total area covered.

Figure 8A:
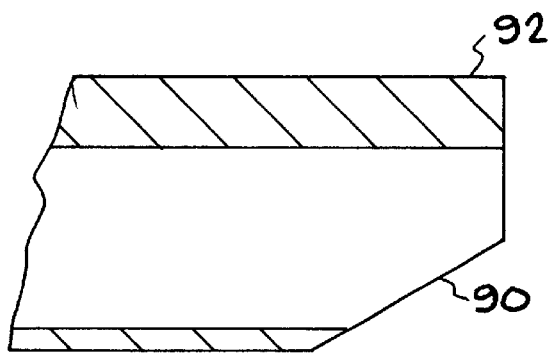
FIGS. 8A–C show an eccentric tip with an off-center flow tube and liquid jetting.
Figure 8B:
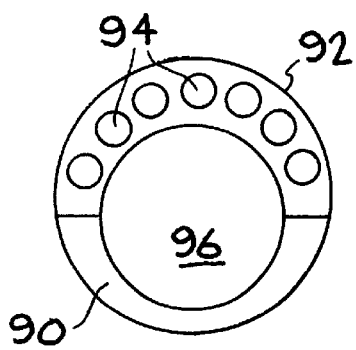
Figure 8C:
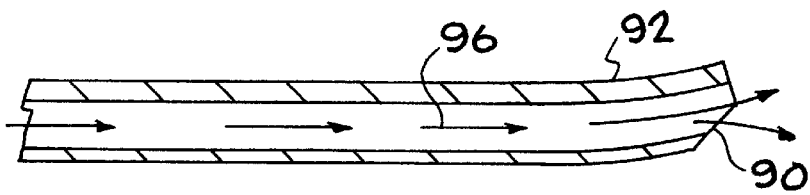

The embodiment of FIG. 8A is similar to that of FIG. 7, but includes a trimmed corner 90 of the delivery system 92, which also contains an off-center construction of the fiber array 94 and the flow tube 96 within delivery system 92, as shown in FIG. 8B. The trimmed corner allows flow to force the assembly to one side. The total area covered depends on the force of the sideways jet and the flexibility of the catheter tip. FIG. 8C illustrates the flow of fluid through the central lumen 96. The fluid flows out of the central lumen with a slight angle due to the trimmed corner 90. The slight angle induced in the fluid flow forces the tip of the catheter or delivery system to bend.

Figure 9:
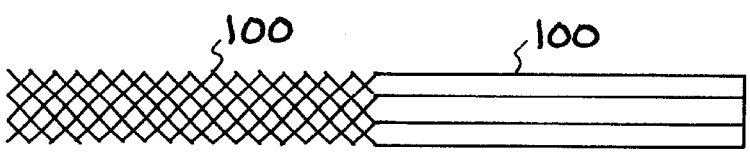
FIG. 9 shows a dual construction delivery system having braided fiber optics at the proximal end and straight fiber optics and the distal end.

The delivery device preferably must traverse through a standard catheter traveling through a tortuous path. Primarily at the distal portion, the device must be flexible, with good column strength for ease of pushing. Toward this end, as shown in FIG. 9, the device may be constructed with fibers 100 (optical or other) incorporated into the wall of the delivery system or catheter (not shown). These embedded fibers can be utilized for desirable characteristics such as cross-woven proximally for strength, and straight threading distally for maximal flexibility, as shown in FIG. 9.

Figure 10:
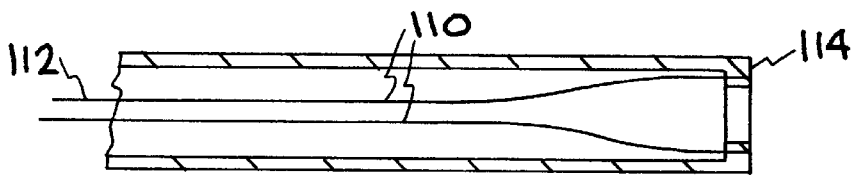
FIG. 10 shows a delivery system where the fibers are free floating within the central lumen and fixed and the distal tip of the delivery system.

Another configuration for decreasing the size of the device and improving flexibility is to allow the fibers to "float" freely within the central lumen throughout the body of the catheter and then fix the fibers at the distal tip. FIG. 10 shows the delivery system having free floating fibers 110 from the proximal end 112 nearly to the distal end, with the fibers 110 attached or fixed in place at the distal tip 114. This embodiment allows the catheter diameter to be reduced if desired and allows for increased flexibility.

Changes and modifications in the specifically described embodiments can be carried out without departing from the scope of the invention, which is intended to be limited by the scope of the appended claims.

What is claimed is:

1. An opto-acoustic recanilization delivery system, comprising:
    a flexible tubing comprising a first end and a second end, wherein said flexible tubing is suitable for insertion into the vasculature and comprises a lumen for flowing a cooling agent; and
    a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed away from said lumen to target areas other than directly forward looking.

2. The opto-acoustic recanilization delivery system of claim 1, wherein said lumen comprises a flexible tubing.

3. The opto-acoustic recanilization delivery system of claim 1, wherein said plurality of optical fibers are arranged concentrically around said lumen to deliver radiation and heat over as large an area as possible.

4. The opto-acoustic recanilization delivery system of claim 1, wherein said flexible tubing comprises a catheter.

5. The opto-acoustic recanilization delivery system of claim 1, wherein each said distal end is beveled or angled to aim the effect (primarily the shock wave) to produce a lateral deviation is said second end upon delivery of laser radiation, or promote a fluid jetting directional phenomena.

6. The opto-acoustic recanilization delivery system of claim 1, wherein said lumen comprises a cooling tip at said second end, wherein said cooling tip comprises a nozzle to allow coolant to jet in particular patterns or directions.

7. The opto-acoustic recanilization delivery system of claim 1, further comprising a second flexible tubing covering said flexible tubing, wherein said plurality of fiber optics, said flexible tubing and said lumen are recessed within said second flexible tubing to form a shrouded tip to prevent said plurality of optical fibers from coming into contact with the wall of said vasculature yet enable light propagated through said plurality of fiber optics to interact with blood or thrombus.

8. The opto-acoustic recanilization delivery system of claim 1, further comprising means for forming an eccentric tip at said second end of said flexible tubing.

9. The opto-acoustic recanilization delivery system of claim 8, wherein said means for forming an eccentric tip at said second end of said flexible tubing are selected from a group consisting of a spring clip, balloon and a protrusion.

10. The opto-acoustic recanilization delivery system of claim 1, further comprising a second flexible tubing covering said flexible tubing, further comprising a spring affixed to the outer wall of said flexible tubing at said second end, wherein said spring is held collapsed within said second flexible tubing, wherein said spring pops up when flexible tubing is extended away from said second flexible tubing to form an eccentric tip.

11. The opto-acoustic recanilization delivery system of claim 1, further comprising a second flexible tubing covering said flexible tubing, further comprising an inflatable bladder affixed to the outer wall of said flexible tubing at said second end, wherein said flexible tubing further comprises at least one leak path between said lumen and said inflatable bladder to present an unobstructed path between said lumen and said bladder, wherein when no cooling flow or other flow is passed though said lumen, said bladder remains deflated, wherein when cooling flow or other flow is passed though said lumen, it passes through said at least one leak path and induces pressure within said bladder causing it to inflate to an eccentric tip.

12. The opto-acoustic recanilization delivery system of claim 1, wherein said plurality of fiber optics comprise an array, wherein said lumen and said array are offset with respect to a central axis of said flexible tubing, to provide an asymmetric construction of said array and said lumen which together forms an eccentric tip.

13. The opto-acoustic recanilization delivery system of claim 11, wherein a corner of said lumen and said flexible tubing are trimmed at an angle, wherein when said cooling agent flows through said lumen, said cooling agent forces said delivery system to move laterally with respect to said central axis of said flexible tubing.

14. The opto-acoustic recanilization delivery system of claim 1, wherein each said proximal end is embedded within said flexible tubing near said first end.

15. The opto-acoustic recanilization delivery system of claim 14, wherein said plurality of optical fibers is braided near said proximal end to provide strength in said delivery system.

16. The opto-acoustic recanilization delivery system of claim 14, wherein said plurality of optical fibers is straight to provide flexibility in said delivery system.

17. The opto-acoustic recanilization delivery system of claim 14, wherein said plurality of optical fibers is braided near said proximal end and wherein said plurality of optical fibers is straight near said distal end to provide flexibility in said delivery system.

18. The opto-acoustic recanilization delivery system of claim 1, wherein said plurality of optical fiber "float" freely within said lumen throughout said lumen until said plurality of fiber optics reach said second end where each said distal end of said plurality of fiber optics is embedded within said flexible tubing.

19. The opto-acoustic recanilization delivery system of claim 1, further comprising a laser for coupling laser light into each said proximal end, wherein said laser light has (i) a pulse frequency within the range of 1 kHz to 100 kHz, (ii) a wavelength within the range of 200 nm to 3000 nm, (iii) a fluence within the range of 0.1 J/cm$^2$ to 300 J/cm$^2$ and (iv) a pulse duration within the range of 1 ns to 1000 ns, wherein said laser light emerges from said distal end to generate an acoustic radiation field in a liquid ambient medium.

20. The opto-acoustic recanilization delivery system of claim 1, further comprising a laser for coupling laser light into each said proximal end, wherein said laser light has (i) a pulse duration within the range of 1 ns to 1000 ns, (ii) an energy per pulse within the range of 10 $\mu$J to 1 mJ, (iii) a wavelength within the range of 200 nm to 3000 nm, (iv) a spot size within the range of 10 $\mu$m to 200 $\mu$m and (v) a repetition rate within the range of 1 kHz to 50 kHz, wherein said laser light emerges from said distal end to generate an acoustic radiation field in a liquid ambient medium.

21. A method of opto-acoustic recanilization, comprising:

inserting an opto-acoustic recanilization delivery system into the vasculature to a point near an occlusion, wherein said opto-acoustic recanilization delivery system comprises a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed away from said lumen to target areas other than directly forward looking; and coupling laser light into said proximal end, wherein said laser light has (i) a pulse frequency within the range of 1 kHz to 100 kHz, (ii) a wavelength within the range of 200 nm to 3000 nm, (iii) a fluence within the range of 0.1 J/cm$^2$ to 300 J/cm$^2$ and (iv) a pulse duration within the range of 1 ns to 1000 ns, wherein said laser light emerges from said distal end to generate an acoustic radiation field in a liquid ambient medium.

22. A method of opto-acoustic recanilization, comprising:

inserting an opto-acoustic recanilization delivery system into the vasculature to a point near an occlusion, wherein said opto-acoustic recanilization delivery system comprises a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed away from said lumen to target areas other than directly forward looking; and coupling laser light into said proximal end, wherein said laser light has (i) a pulse duration within the range of 1 ns to 1000 ns, (ii) an energy per pulse within the range of 10 $\mu$J to 1 mJ, (iii) a wavelength within the range of 200 nm to 3000 nm, (iv) a spot size within the range of 10 $\mu$m to 200 $\mu$m and (v) a repetition rate within the range of 1 kHz to 50 kHz, wherein said laser light emerges from said distal end to generate an acoustic radiation field in a liquid ambient medium.

23. An opto-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking, wherein each said distal end aims the effect to produce a lateral deviation of said second end upon delivery of laser radiation, or promote a fluid jetting directional phenomena.

24. An op to-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking, wherein said lumen comprises a cooling tip at said second end, wherein said cooling tip comprises a nozzle to allow coolant to jet in particular patterns or directions.

25. An opto-acoustic recanilization delivery system, comprising:

a flexible tubing comprising a first end and a second end, wherein said flexible tubing is suitable for insertion into the vasculature and comprises a lumen for flowing a cooling agent;

a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and a second flexible tubing covering said flexible tubing, wherein said plurality of fiber optics, said flexible tubing and said lumen are recessed within said second flexible tubing to form a shrouded tip to prevent said plurality of optical fibers from coming into contact with the wall of said vasculature yet enable light propagated through said plurality of fiber optics to interact with blood or thrombus.

26. An opto-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking, further comprising means for forming an eccentric tip at said second end of said flexible tubing.

27. An opto-acoustic recanilization delivery system, comprising:

a flexible tubing comprising a first end and a second end, wherein said flexible tubing is suitable for insertion into the vasculature and comprises a lumen for flowing a cooling agent;

a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and a second flexible tubing covering said flexible tubing, further comprising a spring affixed to the outer wall of said flexible tubing at said second end, wherein said spring is held collapsed within said second flexible tubing, wherein said spring pops up when said flexible tubing is extended away from said second flexible tubing to form an eccentric tip.

28. An opto-acoustic recanilization delivery system, comprising:

a flexible tubing comprising a first end and a second end, wherein said flexible tubing is suitable for insertion into the vasculature and comprises a lumen for flowing a cooling agent;

a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and a second flexible tubing covering said flexible tubing, further comprising an inflatable bladder affixed to the outer wall of said flexible tubing at said second end, wherein said flexible tubing further comprises at least one leak path between said lumen and said inflatable bladder to present an unobstructed path between said lumen and said bladder, wherein when no cooling flow or other flow is passed though said lumen, said bladder remains deflated, wherein when cooling flow or other flow is passed though said lumen, it passes through said at least one leak path and induces pressure within said bladder causing it to inflate to an eccentric tip.

29. The opto-acoustic recanilization delivery system of claim 28, wherein a corner of said lumen and said flexible tubing are trimmed at an angle, wherein when said cooling agent flows through said lumen, said cooling agent forces said delivery system to move laterally with respect to said central axis of said flexible tubing.

30. An opto-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said proximal end is embedded within said flexible tubing near said first end; wherein each said distal end is embedded within said flexible tubing near said second end; wherein at least one fiber of said plurality of optical fibers at said distal end is pointed towards said lumen to target areas other than directly forward looking wherein said plurality of optical fiber "float" freely within said lumen throughout said lumen until said plurality of fiber optics reach said second end where each said distal end of said plurality of fiber optics is embedded within said flexible tubing.

31. An opto-acoustic recanilization delivery system, comprising:
   a flexible tubing comprising a first end and a second end, wherein said flexible tubing is suitable for insertion into the vasculature and comprises a lumen for flowing a cooling agent;
   a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and
   a laser for coupling laser light into each said proximal end, wherein said laser light has (i) a pulse frequency within the range of 1 kHz to 100 kHz, (ii) a wavelength within the range of 200 nm to 3000 nm, (iii) a fluence within the range of 0.1 J/cm$^2$ to 300 J/cm$^2$ and (iv) a pulse duration within the range of 1 ns to 1000 ns, wherein said laser light emerges from said distal end to generate an acoustic radiation field in a liquid ambient medium.

32. An opto-acoustic recanilization delivery system comprising:
   a flexible tubing comprising a first end and a second end, wherein said flexible tubing is suitable for insertion into the vasculature and comprises a lumen for flowing a cooling agent;
   a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and
   a laser for coupling laser light into each said proximal end, wherein said laser light has (i) a pulse duration within the range of 1 ns to 1000 ns, (ii) an energy per pulse within the range of 10 µJ to 1 mJ, (iii) a wavelength within the range of 200 nm to 3000 nm, (iv) a spot size within the range of 10 µm to 200 µm and (v) a repetition rate within the range of 1 kHz to 50 kHz, wherein said laser light emerges from said distal end to generate an acoustic radiation field in a liquid ambient medium.

33. A method of opto-acoustic recanilization, comprising:
   inserting an opto-acoustic recanilization delivery system into the vasculature to a point near an occlusion, wherein said opto-acoustic recanilization delivery system comprises a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and
   coupling laser light into said proximal end, wherein said laser light has (i) a pulse frequency within the range of 1 kHz to 100 kHz, (ii) a wavelength within the range of 200 nm to 3000 nm, (iii) a fluence within the range of 0.1 J/cm$^2$ to 300 J/cm$^2$ and (iv) a pulse duration within the range of 1 ns to 1000 ns, wherein said laser light emerges from said distal end to generate an acoustic radiation field in a liquid ambient medium.

34. A method of opto-acoustic recanilization, comprising:
   inserting an opto-acoustic recanilization delivery system into the vasculature to a point near an occlusion, wherein said opto-acoustic recanilization delivery system comprises a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein at least one fiber of said plurality of optical fibers at said distal end is pointed towards said lumen to target areas other than directly forward looking; and
   coupling laser light into said proximal end, wherein said laser light has (i) a pulse duration within the range of 1 ns to 1000 ns, (ii) an energy per pulse within the range of 10 µJ to 1 mJ, (iii) a wavelength within the range of 200 nm to 3000 nm, (iv) a spot size within the range of 10 µm to 200 µm and (v) a repetition rate within the range of 1 kHz to 50 kHz, wherein said laser light emerges from said distal end to generate an acoustic radiation field in a liquid ambient medium.

35. An opto-acoustic recanilization delivery system, comprising:
   a flexible tubing comprising a first end and a second end, wherein said flexible tubing is suitable for insertion into the vasculature and comprises a lumen for flowing a cooling agent; and
   a plurality of optical fibers, wherein each fiber of said plurality of optical fibers comprises a proximal end and a distal end, wherein each said distal end is embedded within said flexible tubing near said second end and wherein each said distal end aims the effect to produce a lateral deviation of said second end upon delivery of laser radiation, or promote a fluid jetting directional phenomena.

36. An opto-acoustic recanilization delivery system, comprising:
   a flexible tubing comprising a first end and a second end, wherein said flexible tubing is suitable for insertion into the vasculature and comprises a lumen for flowing a cooling agent;
   a plurality of optical fibers, wherein each fiber of said plurality of optical fibers comprises a proximal end and a distal end, wherein each said distal end is embedded within said flexible tubing near said second end further comprising a second flexible tubing covering said flexible tubing; and
   a spring affixed to the outer wall of said flexible tubing at said second end, wherein said spring is held collapsed within said second flexible tubing, wherein said spring pops up when said flexible tubing is extended away from said second flexible tubing to form an eccentric tip.

37. An opto-acoustic recanilization delivery system, comprising:
   a flexible tubing comprising a first end and a second end, wherein said flexible tubing is suitable for insertion into the vasculature and comprises a lumen for flowing a cooling agent;

a plurality of optical fibers, wherein each fiber of said plurality of optical fibers comprises a proximal end and a distal end, wherein each said distal end is embedded within said flexible tubing near said second end further comprising a second flexible tubing covering said flexible tubing; and a second flexible tubing covering said flexible tubing, further comprising an inflatable bladder affixed to the outer wall of said flexible tubing at said second end, wherein said flexible tubing further comprises at least one leak path between said lumen and said inflatable bladder to present an unobstructed path between said lumen and said bladder, wherein when no cooling flow or other flow is passed though said lumen, said bladder remains deflated, wherein when cooling flow or other flow is passed though said lumen, it passes through said at least one leak path and induces pressure within said bladder causing it to inflate to an eccentric tip.

38. The opto-acoustic recanilization delivery system of claims 37, wherein a corner of said lumen and said flexible tubing are trimmed at an angle, wherein when said cooling agent flows through said lumen, said cooling agent forces said delivery system to move laterally with respect to said central axis of said flexible tubing.

39. An opto-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein each said proximal end is embedded within said flexible tubing near said first end and wherein said plurality of optical fibers is braided near said proximal ends and wherein said plurality of optical fibers is straight near said distal ends to provide flexibility in said delivery system.

40. An opto-acoustic recanilization delivery system, comprising:

a flexible tubing comprising a first end and a second end, wherein said flexible tubing is suitable for insertion into the vasculature and comprises a lumen for flowing a cooling agent; and a plurality of optical fibers, wherein each fiber of said plurality of optical fibers comprises a proximal end and a distal end, wherein each said distal end is embedded within said flexible tubing near said second end and wherein said plurality of optical fiber "float" freely within said lumen throughout said lumen until said plurality of fiber optics reach said second end where each said distal end of said plurality of fiber optics is embedded within said flexible tubing.

41. The opto-acoustic recanilization delivery system of claim 1, wherein each said distal end aims the effect to produce a lateral deviation of said second end upon delivery of laser radiation, or promote a fluid jetting directional phenomena.

42. The opto-acoustic recanilization delivery system of claim 26, wherein each said distal end aims the effect to produce a lateral deviation of said second end upon delivery of laser radiation, or promote a fluid jetting directional phenomena.

43. The opto-acoustic recanilization delivery system of claim 27, wherein each said distal end aims the effect to produce a lateral deviation of said second end upon delivery of laser radiation, or promote a fluid jetting directional phenomena.

44. The opto-acoustic recanilization delivery system of claim 36, wherein each said distal end aims the effect to produce a lateral deviation of said second end upon delivery of laser radiation, or promote a fluid jetting directional phenomena.

45. The opto-acoustic recanilization delivery system of claim 32, wherein each said distal end aims the effect to produce a lateral deviation of said second end upon delivery of laser radiation, or promote a fluid jetting directional phenomena.

46. The opto-acoustic recanilization delivery system of claim 36, wherein each said distal end aims the effect to produce a lateral deviation of said second end upon delivery of laser radiation, or promote a fluid jetting directional phenomena.

47. The opto-acoustic recanilization delivery system of claim 39, wherein each said distal end aims the effect to produce a lateral deviation of said second end upon delivery of laser radiation, or promote a fluid jetting directional phenomena.

48. The opto-acoustic recanilization delivery system of claim 41, wherein each said distal end aims the effect to produce a lateral deviation of said second end upon delivery of laser radiation, or promote a fluid jetting directional phenomena.

* * * * *

UNITED STATES PATENT AND TRADEMARK OFFICE
CERTIFICATE OF CORRECTION

PATENT NO. : 6,368,318 B1
DATED : April 9, 2002
INVENTOR(S) : Steven R. Visuri et al.

It is certified that error appears in the above-identified patent and that said Letters Patent is hereby corrected as shown below:

<u>Title page,</u>
Assignee should read as follows:
-- [73] Assignee: The Regents of the University of California, Oakland, CA (US)

EndoVasix, Inc., Belmont, CA (US) --

Signed and Sealed this

Ninth Day of July, 2002

*Attest:*

JAMES E. ROGAN
*Attesting Officer*         *Director of the United States Patent and Trademark Office*